United States Patent [19]

Meier et al.

[11] Patent Number: 5,496,803
[45] Date of Patent: Mar. 5, 1996

[54] PROCESS FOR THE LONG TERM REDUCTION OF BODY FAT STORES, INSULIN RESISTANCE, HYPERINSULINEMIA IN VERTEBRATES

[75] Inventors: Albert H. Meier; Anthony H. Cincotta, both of Baton Rouge, La.

[73] Assignee: Louisiana State University and Agricultural and Mechanical College, Baton Rouge, La.

[21] Appl. No.: 287,066

[22] Filed: Aug. 8, 1994

Related U.S. Application Data

[63] Continuation of Ser. No. 999,685, Dec. 31, 1992, abandoned, which is a continuation of Ser. No. 192,332, May 10, 1988, abandoned.

[51] Int. Cl.$^6$ .............................. C07K 14/64; C07K 9/00; A61K 38/00
[52] U.S. Cl. ..................................... 514/12; 514/3; 514/4
[58] Field of Search ........................................ 514/3, 4, 12

[56] References Cited

PUBLICATIONS

Meier et al., *Biology of Reproduction* 8:400–410, 1973.
Meier et al., *General and Comparative Endocrinology* 26:253–258, 1975.
Meier et al., *General and Comparative Endocrinology* Suppl. 3:499–508, 1972.
Barnett, *Post Graduate Medical J.* 56:11–14, 1980.
Meier et al., *Current Ornithology* 2:303–343, 1984.
Cincotta, *J. Endocrinol.* 106:173–176, 1984.
Wilson, *Chrono. Bio. Int.* 6:113–121, 1989.
Cincotta et al., *J. Endocrinol.* 120:385–391, 1989.
Albert H. Meier and Albert C. Russo, Circadian Organization of the Avian Annual Cycle, pp. 316, 326–T, 328–9, 330, 1973.
Christopher J. deSouza and Albert G. Meier, Circadian and Seasonal Variations of Plasma Insulin and Cortisol Concentrations in the Syrian Hamster, Mesocricetus Auratus, vol. 4, No. 2, pp. 141–151, 1987 Chronobiology International.
Albert H. Meier, Temporal Synergism of Prolactin and Adrenal Steroids, General and Comparative Endocrinology Supplement 3, 499–508 (1972).
Albert H. Meier and John T. Burns, Circadian Hormone Rhythms in Lipid Regulation, Amer. Zool., 16:649–659 (1976).
E. Bonora, C. Coscelli and U. Butturini, Relationship between Insulin Resistance, Insulin Secretion and Insulin Metabolism in Simple Obesity, International Journal of Obesity (1985) 9, 307–312.
C. Ronald Kahn, M.D., Insulin Resistance: A Common Feature of Diabetes Mellitus, The New England Journal of Medicine, Jul. 24, 1986.
Mayer B. Davidson, MD., Review: Pathogenesis of Type 2 Diabetes Mellitus: An Interpretation of Current Data, The American Journal of the Medical Sciences Jul. 1986 vol. 292 No. 1.
Joseph A. Truglia, M.D., James N. Livingston, D.V.M., Ph.D., Dean H. Lockwood, M.D., Insulin Resistance: Receptor and Post Binding Defects in Human Obesity and Non–Insulin–Dependent Mellitus, The American Journal of Medicine vol. 979 (Suppl 2B) Aug. 23, 1985.
Steven M. Haffner, M.D., Michael P. Stern, M.D., Helen P. Hazuda, Ph.D., Jacqueline A. Pugh, M.D., and Judith K, Patterson, Ph.D. Hyperinsulinemia in a Population at High Risk for Non–Insulin–Dependent Diabetes Mellitus, The New England Journal of Medicine, Jul. 24, 1986.
Cincotta et al., *J. of Endocrinology*, 120, 385–391, 1989.
Odedra et al., *Chem. Absts.*, 97, 79, 1982, entry No. 104402z.
Iida, *Chem. Absts.*, 75, 82, 1971, entry No. 30764t.
Cincotta et al. Chronobiology International, vol. 10, No. 4, pp. 244–258 (1993).
Ojasoo et al. Steroid Hormone Receptors in Comprehensive Medicinal Chemistry, Hansch et al., eds., vol. 3, pp. 1213–1218 (1990).

*Primary Examiner*—Jill Warden
*Assistant Examiner*—Lynn Touzeau
*Attorney, Agent, or Firm*—Darby & Darby

[57] ABSTRACT

A process for the long-term modification and regulation of lipid metabolism— generally to reduce obesity, insulin resistance, and hyperinsulinemia (the three hallmarks of Type II diabetes)—by injections into the bloodstream of a vertebrate, animal or human, of prolactin, or both prolactin and a glucocorticosteroid. The injections are made over a limited period at a time of day dependent on the normal circadian rhythm of fat and lean members of a similar species. Decreases (or increases) in body fat deposits result by treatment of an obese species (lean species) on a daily timed sequence based on circadian rhythms of the peak prolactin, or peak prolactin and peak glucocorticosteroid, blood level established for lean members (or obese members) of a similar species. Insulin resistance, and hyperinsulinemia can also be controlled in humans on a long-term basis by treatment corresponding to that of the treatment for obesity. The short-term daily injections reset hormonal timing in the neural centers of the brain to produce long-term effects.

13 Claims, No Drawings

PROCESS FOR THE LONG TERM REDUCTION OF BODY FAT STORES, INSULIN RESISTANCE, HYPERINSULINEMIA IN VERTEBRATES

This is a continuation of application Ser. No. 07/999,685, filed Dec. 31, 1992 and now abandoned, which is a continuation of Ser. No. 07/192,332 filed Jun. 10, 1988 and now abandoned.

FIELD OF THE INVENTION

This invention relates to a process for the reduction in animals, and humans, of body fat stores, and reduction of insulin resistance, as well as hyperinsulinemia, which is often associated with insulin resistance. In particular, it relates to timed hormonal injections to reduce and control over an extended period high insulin resistance which, with obesity and hyperinsulinemia, are pathologies characteristic of the onset of Type II diabetes.

BACKGROUND

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications, and diabetes and its complications are a leading cause of death in this country.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally burned in the liver to $CO_2$ and $H_2O$ (50%); 5% to glycogen, and 30 to 40% to fat, which is stored in fat depots. Fatty acids are circulated, returned to the liver and metabolized to ketone bodies for utilization by the tissues. The fatty acids are also metabolized by other organs, fat formation being a major pathway for for carbohydrate utilization. The net effect of insulin is to promote the storage and use of carbohydrate, protein and fat. Insulin deficiency is a common and serious pathologic condition in man. In Type I diabetes the pancreas produce little or no insulin, and insulin must be injected daily for the survival of the diabetic. In Type II diabetes the pancreas produces some insulin, but the amount of insulin is insufficient, or less than fully effective due to cellular resistance, or both. In either form there are widespread abnormalities, but the fundamental defects to which the abnormalities can be traced are (1) a reduced entry of glucose into various "peripheral" tissues and (2) an increased liberation of glucose into the circulation from the liver (increase hepatic glucogenesis). There is therefore an extracellular glucose excess and an intracellular glucose deficiency which has been called "starvation in the midst of plenty." There is also a decrease in the entry of amino acids into muscle and an increase in lipolysis. Thus, there results, as a result of the diabetic condition, elevated levels of glucose in the blood, and prolonged high blood sugar is indicative of a condition which will cause blood vessel and nerve damage. Obesity, or excess fat deposits, it is believed may trigger the onset of diabetes by increasing cellular resistance to insulin. Prior to the onset of diabetes, the pancreas of the obese are taxed to produce additional insulin; but eventually, perhaps over several years, insulin productivity falls and diabetes results. Reduction of body fat can improve insulin production, and it is thought avoid cellular insensitivity to insulin. The reduction of body fat stores on a long term, or permanent basis in domestic animals would obviously be of considerable economic benefit to man, particularly since animals supply a major portion of man's diet; and the animal fat may end up as de novo fat deposits in man. The reduction of body fat stores in man likewise would be of significant benefit, cosmetically and physiologically. Indeed, obesity, and insulin resistance, the latter of which is generally accompanied by hyperinsulinemia, are the three hallmarks of Type II diabetes. Whereas controlled diet and exercise can produce modest results in the reduction of body fat deposits, no effective treatment has been found for controlling either hyperinsulinemia, or insulin resistance. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also found in the setting defined by higher-than-normal levels of insulin—i.e., hyperin-sulinemia— when there is present normal or elevated levels of blood glucose. Despite decades of research on these serious health problems, the etiology of obesity and insulin resistance is unknown.

The principal unit of biological time measurement, the circadian or daily rhythm, is present at all levels of organization. Daily rhythms have been reported for many hormones inclusive of the adrenal steroids, e.g., the glucocorticosteroids, notably cortisol, and prolactin, a hormone secreted by the 1 pituitary. In an early article, discussing the state-of-the-art at that time, it is reported that "Although correlations have been made between hormone rhythms and other rhythms, there is little direct evidence that the time of the daily presence or peak level of hormones has important physiological relevance." See *Temporal Synergism of Prolactin and Adrenal Steroids* by Albert H. Meier, General and Comparative Endocrinology, Supplement 3, 1972 Copyright 1972 by Academic Press, Inc. The article then describes arian physiological responses to prolactin injections given over daily periods. These responses include increases and decreases in body fat stores, dependent on the time of day of the injection and season, the season being a determinant of normal high body weight and consequent high fat stores or low body weight and consequent low fat stores within the animal. Prolactin was thus found to stimulate fattening only when injected at certain times of the day, and the time of the response to prolactin was found to differ between lean animals and fat animals. In an article titled *Circadian and Seasonal Variation of Plasma Insulin and Cortisol Concentrations in the Syrian Hamster, Mesocricetus Auratus* by Christopher J. de Souza and Albert H. Meier, Chronobiology International, Vol. 4, No. 2, pp 141–151, 1987, there is reported a study of circadian variations of plasma insulin and cortisol concentrations in scotosensitive and scotorefractory Syrian hamsters maintained on short and long periods of daylight to determine possible seasonal changes in their daily rhythms. The baseline concentration of insulin was found to be greater in female than in male scotosensitive hamsters on short daylight periods. These differences it is reported, may account for the observed heavy fat stores in female and low fat-stores in male scotosensitive hamsters kept on short daylight periods. The plasma concentrations of both cortisol and insulin varied throughout the day for the groups of animals tested, but were not equivalent. The circadian variations of cortisol were similar irrespective of sex, seasonal condition and daylight. The circadian variation of insulin, in contrast, differed markedly. Neither the daily feeding pattern or glucose concentration varied appreciably with seasonal condition, or daylight. The time of day, or the season, it is reported do not appear to affect the concentations in glucose or cortisol levels. It is postulated that the daily rhythms of cortisol and insulin are regulated by different neural pacemaker systems, and that changes in the phase relations of circadian systems account in part for seasonal changes in body fat stores. The circadian rhythms of prolaotin and the glucocorticosteroid hormones, e.g., cortisol, have thus been perceived as having important though far from fully understood roles in regulating daily and seasonal changes in body fat stores and in the organization and integration of total animal metabolism. See *Circadian Hormone Rhythms in Lipid Regulation*, by Albert H. Meier and John T. Burns, Amer. Zool. 16:649–659 (1976).

OBJECTS

It is the primary objective of the present invention to provide a process, or method, for regulating, and resetting on a long term basis the circadian hormonal rhythms which regulate the lipid metabolism of vertebrates, i.e., animals, including humans.

In particular, it is an object to provide a process for resetting the circadian neural centers of animals, including humans, to produce long lasting changes in the amount of body fat stores, the sensitivity of the cellular response of a species to insulin, and overcome hyperinsulinemia which generally accompanies insulin resistance.

A more specific object is to provide a process for resetting the circadian neural centers of animals, including humans, to decrease obesity and maintain the more normal body fat stores of a lean animal, or lean human, on a long term basis.

A further, and equally specific object is to provide a process for resetting on a long term basis the circadian neural centers, particularly in humans, to increase or improve the sensitivity and responsiveness of the cells to insulin, and suppress hyperinsulinemia.

SUMMARY OF THE INVENTION

These objects and others are achieved in accordance with the present invention, characterized as a process, or method, for the regulation of lipid metabolism to produce long term, lasting, and permanent effects by the use of timed daily injections into the bloodstream of a vertebrates, animal or human, of prolactin, or prolactin and a glucocorticosteroid, notably cortisol. Injections of prolactin, or prolactin and glucocorticosteroid, are continued on a daily basis for a period sufficient to reset the phase oscillation of the prolactin rhythm, or oscillations of both the prolactin and glucocorticosteroid rhythms which are expressions of the prolactin and glucocorticosteroid neural oscillations, respectively. The phase relationship of the prolactin oscillation, and preferably both neural oscillations are modified and reset such that, on cessation of the daily injections of the prolactin, or prolactin and glucocorticosteroid, the lipid metabolism of the animal, or human, continues over a long term period, if not permanently, at the altered metabolic setpoint, or setpoints.

DESCRIPTION OF THE PREFERRED EMBODIMENT

In the treatment of an animal, or human subject, the stores of body fat can be depleted or increased, the treatments continued until the stores of body fat are stabilized at an optimum or near-optimum level dependent on the level of body fat stores desired in the subject, and for time sufficient that on termination of the treatment the prolactin rhythm, and preferably both the prolactin and glucocorticosteroid rhythms have been reset to maintain on a long term basis the reduced, or increased, body weight stores. In humans, the objective is almost invariably to reduce body fat stores, and obesity. It has been established that a relationship exists between obesity and insulin resistance, and that obesity can lead to increased insulin resistance. Likewise, it has been established that the circadian rhythms of plasma prolactin and gluoocorticosteroid concentrations, respectively, have important consequences in the regulation of body fat stores, and that the phase relationship between the prolactin and glucocorticosteroid levels, respectively, differ in lean and fat animals. In a fat animal prolactin will reach a peak level at a given hour of a 24 hour period (in a human usually at night), and the prolactin level of a lean animal at another time of day (in a human usually at mid morning). In a lean animal the glucocorticosteroids, e.g., cortisol, will peak during a 24 hour period at a given hour (generally at a time different from that of prolactin; and in a human generally several hours after waking. Thus, the phase relations of the cortisol and prolaotin rhythms differ in lean and fat animals. The peak periods of prolactin and glucocorticosteroid production, respectively, may differ to some extent between male and females of any given species. This being so, it has been found that daily injections of prolactin, preferably daily injections of both prolactin and glucocorticosteroid, respectively, be made into the blood of an obese subject at the normal time of day that the prolaotin, or prolactin and glucocorticosteroid, respectively, would be at their peaks in a lean subject of the same species and sex. Such treatment will, if continued over a sufficient period reset on a long term or permanent basis the phase of the neural oscillation for the prolactin rhythm, or the phases of the neural oscillations for both the prolactin and glucocorticosteroid rhythms in the obese individual to that present in a lean subject. The obese subject, on initiation of the treatment with prolactin, preferably prolactin and glucocorticosteroid, respectively, will lose body fat stores, and the body fat deposits of the obese subject on continuation of the treatments on a daily basis will drop to and stabilize at that of a lean subject of the same species. On discontinuing the daily treatments, the rise and fall of the prolactin, or prolactin and gluoocorticosteroid levels in the blood of the treated patient on a daily basis will correspond to that of a lean subject of the same species, and for a period of long duration. The effect of resetting the prolactin, or prolactin and glucocorticosteroid rhythms, in this manner also increases the sensitivity of the cells of the subject to insulin, reduces hyperinsulinemia, and thus alters long term pathologies which are characteristics of the onset of Type II diabetes.

In vertebrates, injections of prolactin given once a day on a daily basis, generally over a period ranging from about 5 days to about 10 days, at levels ranging from about 175 micrograms to about 2000 micrgrams, per pound of body weight, are adequate to reset the circadian plasma prolactin rhythm. Preferably, however, in treating humans, a prolactin daily dosage is injected at one given hour, and a daily glucocorticosteroid dosage at another during the same 24 hour period. The glucocorticosteroid, suitably and preferably cortisol, is given on a daily basis suitably at a dosage level ranging from about 175 micrograms to about 2000 micrograms, per pound of body weight. Such treatments over a period of about 5 to about 10 days, preferably daily dosages of both prolactin and a glucocorticosteroid, given to an obese person at times corresponding to times during the 24 hour period, or circadian cycle, when the prolactin and gluoocorticosteroid concentrations peak in a lean person will modify and reset the lipid metabolism of the obese person to that of a lean person. Body fat deposits within the obese person will be reduced, levelled out and maintained after the treatments are discontinued at that of a lean person, over an extended period of time. A lean or obese person showing the effects of insulin resistance, or hyperinsulinemia, or both insulin resistance and hyperinsulinemia, treated with prolactin and a glucocorticosteroid, in the same manner as a person suffering with obesity, will become more sensitive to insulin (i.e., will have a lower insulin resistance), and the effects of hyperinsulinemia will be reduced on a long term basis. The injections of prolactin and a glucocorticosteroid will thus reset the phase relations of the two neural oscillations and their multiple circadian expressions to alter metabolism on a long term, if not permanently. In other words, there will be as a result of the timed daily hormonal injections a long term reversal of the major pathologies generally associated with the development of Type II diabetes. The levels of body fat stores, or plasma insulin concentrations and insulin resistance, or all of these pathologies can be reduced on a long term basis by such treatment, or treatments, from the high levels often found in obese, hyperinsulinemiac persons to that of the much lower and more desirable levels found in lean persons.

In terms of the human subject, "obesity can be defined as that body weight over 20 percent above the ideal body weight for a given population" (R. H. Williams, Textbook of Endocrinology, 1974, p. 904–916.). The time of day when the prolactin and glucocorticosteroid levels, respectively, will peak in the blood of humans during a day differs between obese subjects and lean subjects, and the peak in each type of subject can be readily determined by measurement of the fat and lean specimens, as defined. In other animal species what constitutes obese and lean members, respectively, of a species can be readily determined by body weight patterns correlated with the prolaotin and gluoocorticosteroids levels, respectively, in the plasma of the lean and obese members, respectively. The levels differ between members of the different species, but among members of the same species there is close correlation between the prolactin and glucocorticosterone levels, respectively, at certain times of the day dependent on the obesity or leanness of a given specimen.

These and other features of the invention will be better understood by reference to the following information and data of experimental work with animals done on a comparative basis. In the examples the terminology "LD" refers to the light/dark cycle, the first number following the expression LD refers to the hours of light, and the second to the hours of darkness in the cycle. Thus LD 14:10 refers to a cycle having 14 hours of light and 10 hours of darkness, and the period of a day is expressed in terms of 2400 hours. The letter n refers to the number of animals in a group, "BW" designates body weight, g represents grams and "ug" is an expression of micrograms.

EXAMPLE 1

Adult (135–150 g) female Syrian hamsters (*Mesocricetus auratus*) were raised on 14-hour daily photoperiods (LD 14:10) from birth (4–12 months). After adaptation to continuous light for 14 days, two groups (n=8) were injected (i.p.) daily for 10 days with cortisol (75 ug/100 g B.W/day) and prolactin (75 ug/100 g B.W/day). One group (0-hour treatment group) received the prolactin injections at the same time of day (2000) as the cortisol injections whereas the other treatment group (12-hour group) received prolactin 12 hours after the cortisol injections. This treatment is thought to produce two different phase relations between two circadian neuroendocrine oscillations. Two additional control groups (n=8) received daily injections of saline alone in the 0-hour and 12-hour relations.

After the injection period, the animals were transferred from continuous light to LD 12:12 (light onset:0800) where they remained under normal laboratory conditions (room temperature and ad libitum feed and water) for 10 weeks when the animals were examined. Such photoperiodic treatment produces obesity and hyperinsulinemia in untreated female hamsters.

To account for circadian variations in plasma insulin concentration, plasma glucose concentration and hypoglycemic responsiveness to insulin, blood samples were taken (orbital sinus puncture) from 2 animals within each group at 6 hourly intervals (0800, 1400, 2000, 0200). These samples were centrifuged at 1500 g for 25 minutes and the plasma was stored at $-20°$ C. until assayed for hormone and glucose concentrations. Fifteen minutes after the initial sampling, each animal was injected (i.p.) with bovine insulin (20 mU/100 g B.W.). Thirty minutes after the insulin injections, blood was again drawn from the orbital sinus, centrifuged, and the plasma stored to determine later the hypoglycemic response to exogenous insulin. The animals were subsequently sacrificed by an overdose of sodium pentobarbital, and the abdominal fat was removed and weighed as an index of body fat stores.

Plasma glucose concentration was determined enzymatically by glucose oxidase (Sigma Diagnostic Bulletin No. 315) from blood drawn before and after insulin treatment. Plasma insulin concentration was determined only on the pretreatment samples. The insulin radioimmunoassay employed radiolabelled porcine insulin and guinea pig antisera (Cambridge Diagnostics Billerica, Mass., U.S.A.), as previously described.

Because the hypoglycemic response to exogenous insulin may he complex and involve counter regulatory hormones, pretreatment and posttreatment plasma samples were also assayed for cortisol and glucagon concentrations.

TABLE 1

Effects of timed prolactin and cortisol injections upon body fat stores, plasma insulin, plasma glucose, and insulin resistance from Example 1.

|  | Saline | Prolactin 0h after Cortisol | Prolactin 12h after Cortisol |
| --- | --- | --- | --- |
| (n) | 16 | 8 | 8 |
| Body Weight (% increase over injection period) | 17 ± 4 | 16 ± 9 | 26 ± 9 |
| Retroperitoneal Fat Weight (g) | 5.3 ± 0.5 | 3.2 ± 0.2 | 7.0 ± 0.3 |
| Retroperitoneal Fat Weight | 3.2 ± 0.3 | 2.2 ± 0.2 | 3.9 ± 0.1 |

TABLE 1-continued

Effects of timed prolactin and cortisol injections upon body fat stores, plasma insulin, plasma glucose, and insulin resistance from Example 1.

|  | Saline | Prolactin 0h after Cortisol | Prolactin 12h after Cortisol |
| --- | --- | --- | --- |
| (% B.W.) |  |  |  |
| Plasma insulin (mU/l) | 85 ± 18 | 44 ± 6 | 76 ± 6 |
| Plasma glucose (m mol/l) | 3.88 ± 0.16 | 3.77 ± 0.28 | 4.44 ± 0.11 |
| Insulin/ glucose (units/ mole) | 21.9 ± 4.7 | 11.7 ± 1.8 | 17.2 ± 1.6 |
| Hypoglycemic response to exogenous insulin (0.2U/kg B.W.) (% decrease in plasma glucose) | 0 ± 0 | 12 ± 6 | 0 ± 0 |

Example 2

A second experiment was performed to retest the results of Example 1. The two experimental protocols were similar; however, three changes were made in this experiment. 1.) The animals were younger (3–6 months of age) and weighed less (90–100 g) at the time of cortisol and prolactin treatment. 2.) All blood samples were drawn at a single time of day (0800). 3.) the insulin dose (200 u/100 g B.W.) was greater. Statistical differences between groups were determined and are given in Table 2 as follows.

TABLE 2

Effects of timed prolactin and cortisol injections upon body fat stores, plasma insulin, plasma glucose, and insulin resistance from Example 2.

|  | Saline | Prolactin 0h after Cortisol | Prolactin Rh after Cortisol |
| --- | --- | --- | --- |
| (n) | 8 | 4 | 4 |
| Body Weight (% increase over injection period) | 56 ± 4 | 43 ± 2 | 58 ± 2 |
| Food Consumption (g/animal/day) | 9.1 ± 0.2 | 7.9 ± 0.1 | 9.2 ± 0.2 |
| Retroperitoneal Fat Weight (g) | 7.0 ± 0.6 | 3.2 ± 0.3 | 6.6 ± 0.4 |
| Retroperitoneal Fat Weight (% B.W.) | 3.9 ± 0.2 | 2.3 ± 0.3 | 3.9 ± 0.3 |
| Plasma insulin (mU/l) | 96 ± 16 | 29 ± 3 | 64 ± 18 |
| Plasma glucose (m mol/l) | 4.33 ± 0.16 | 4.05 ± 0.28 | 4.27 ± 0.22 |
| Insulin/ glucose (units/ mole) | 21.9 ± 3.5 | 7.1 ± 0.3 | 14.3 ± 3.2 |
| Hypoglycemic response to exogenous insulin (0.2U/kg B.W.) (% decrease in plasma glucose) | 29 ± 5 | 53 ± 3 | 39 ± 7 |

Comparison of the two sets of experimental data show that the abdominal fat weights, plasma insulin concentrations and plasma glucose concentrations were similar in the two saline injected control groups ten weeks following the injections, and the two groups were combined for comparison with the two hormone-treated groups (Table 1). Injections of prolactic 12 hours after daily injections of cortisol were ineffective. None of the parameters examined differed significantly from control levels. However, the 0-hour relation of cortisol and prolactin injections dramatically altered fat weights and plasma insulin concentration determined ten weeks after treatment. Compared with control levels, the 0-hour treatment reduced ($p<0.05$) abdominal fat weight by 41% and plasma insulin concentration by 48% ($p<0.05$). Because plasma glucose concentration was not altered relative to control levels, the 0-hour relation also reduced the insulin to glucose ratio (48%, $p<0.05$).

Insulin administration did not reduce plasma glucose concentration within 30 minutes in either saline-injected control groups nor in the 12-hour hormone-treatment group, perhaps in part because of the low insulin dose (20 mV/100 g B.W.). However, the 0-hour relation of cortisol and prolactin injections reduced plasma glucose levels by 12% ($p<0.05$).

The results given in Example 2 were similar to those observed in Example 1 (Table 2). The abdominal fat weights, plasma insulin concentrations and plasma glucose concentrations were all similar 20 weeks following treatment in the two saline-injected control groups as well as in the 12-hour hormone-injected group. However, as in Example 1, the 0-hour cortisolprolactin treatment reduced abdominal fat weight (55%, $p<0.05$) and plasma insulin concentration (70%, $p<0.05$) without a significant change in plasma glucose concentration. The insulin to glucose ratio was reduced by 67% ($p<0.05$). Furthermore, only the 0-hour cortisol-prolactin group reduced total food consumption (13%, $p<0.05$) and body weight gain (23%, $p<0.05$) compared with saline-injected control levels during the ten weeks following treatment.

The higher dose of insulin used in Example 2 (200 mU/100 g B.W.) reduced plasma glucose concentrations in both saline-injected groups and in both hormone-injected groups (Table 2). However, only the 0-hour cortisol-prolactin treatment and not the 12-hour treatment produced a greater hypoglycemic effect compared with the controls. The 0-hour hormone treatment reduced plasma glucose by 53% compared with a 29% reduction in the controls ($p<0.05$).

In this regard, it must be noted that the assessment of insulin resistance is a complex problem, and several elaborate methodologies have been designed (such as the euglycemic clamp technique) to accurately quantitate sensitivity to the hypoglycemic effects of insulin. The simplest way to assess the in vivo action of insulin is to determine the fall in plasma glucose level that occurs after administration of exogenous insulin. The major drawback with this approach is that counter regulatory hormones may be secreted in response to insulin-induced hypoglycemia. Thus, the glucose level after insulin administration may reflect an interplay between several hormones and not a straight forward response to insulin. However, assays of cortisol and glycogen before and after insulin administration demonstrate that these hormones cannot account for the group differences in hypoglycemic responsiveness to insulin. In other words, the decreased hypoglycemic responsiveness to insulin in the control and 12-hour treatment groups relative to the 0-hour treatment group is not associated with relatively higher cortisol and glucagon levels after the insulin injection.

Lastly, the plasma insulin to glucose ratio can be used as a relative index of insulin resistance. The relative group differences in insulin to glucose ratio corroborate the relative group differences in hypoglycemic responsiveness to exogenous insulin. Compared with controls, the 0-hour hormone treated animals need 48 to 70% less endogenous insulin to maintain the same plasma glucose level (Tables 1 and 2).

The data show treatment of an animal to produce a long term reversal of major pathologies generally associated with the development of Type II diabetes. The magnitude of the reversal induced by the 0-hour relation of cortisol and prolactin injections was dramatic and nearly complete 10 weeks following hormone treatment. The levels of body fat stores, plasma insulin concentrations and insulin resistance were reduced by cortisol-prolactin treatment from the high levels found in obese, hyperinsulinemic hamsters to the much lower levels found in lean, normal littermates (Table 1).

The data show that metabolic states are regulated at least in part by an interaction of circadian neuroendocrine rhythms. This hypothesis proposes that the daily rhythms of cortisol and prolactin are individual expressions of two separate circadian systems and that the daily injections of these hormones can reset the phase relations of these two systems. Thus, the 0-hour relation resets the circadian oscillations into a pattern that maintains the lean, insulin sensitive state and the 12-hour relation permits retention of a pattern that maintains the obese, insulin resistant state. Another important addition of the present study is that the effects of timed injections of cortisol and prolactin are long lasting. Apparently once reset, the phase relation of the two circadian oscillations tends to maintain its altered pattern.

Changes in the phase relations of two circadian neuroendocrine oscillations are evidenced by changes in the phase relations of their circadian expressions. This expectation is fulfilled respecting plasma glucocorticosteroid and prolactin rhythms. In several species examined, including Syrian hamsters, the phase relations of the two hormone rhythms differ in lean and fat animals.

The phase relation between the circadian rhythm of plasma insulin concentration and the rhythm of lipogenic responsiveness to insulin is shown to differ in lean and fat hamsters. Whereas the daily interval of lipogenic responsiveness remains near light onset, the phase of the insulin rhythm varies markedly. The peak concentration of insulin occurs near light onset in obese female hamsters held on short daylengths. That is, the daily peaks of the lipogenic stimulus (i.e., insulin) and the lipogenic response to insulin coincide in fat hamsters and not in lean hamsters.

The phase relations of both prolactin and insulin rhythms as well as the rhythms of tissue responses to the hormones are important elements in the regulation of lipogenesis. All of these rhythms, then, would be phase adjusted to regulate lipogenesis. Phase adjustment of these and perhaps other rhythms may also account for insulin resistance.

It is apparent that various modifications and changes can be made without departing the spirit and scope of this invention.

Having described the invention, what is claimed is:

1. A method for modifying or resetting the phases of circadian oscillations of the brain which control circadian rhythms of prolactin levels in the bloodstream of said patient in need of the modification and resetting comprising administering prolactin into the blood stream of said patient on a daily basis (i) at a time within the daily interval at which the prolactin level in the bloodstream of a lean insulin-sensitive human reaches its peak value and (ii) in an amount sufficient to increase the sensitivity of the patient to insulin;

continuing the daily administration of prolactin for a period of time sufficient to modify or reset the patient's daily prolactin level cycle so that said cycle mimics in phase and amplitude the daily prolactin level cycle of a lean insulin-sensitive human.

2. The method of claim 1 wherein the modification persists after cessation of said prolactin administration.

3. The method of claim 1 further comprising administering a glucocorticosteroid to said patient.

4. The method of claim 3 wherein said glucocorticosteroid is administered daily at a second predetermined time of day, said second time being within the daily time interval at which the glucocorticosteroid level of lean insulin-sensitive human reaches its peak value.

5. The method of claim 1 wherein prolactin is administered once a day at dosage levels ranging from about 175 micrograms to about 2000 micrograms, per pound of body weight.

6. The method of claim 4 wherein the prolactin is administered at dosage levels ranging from about 175 micrograms to about 2000 micrograms per pound body weight, and glucocorticosteroid is administered at dosage levels ranging from about 175 micrograms to about 2000 micrograms, per pound of subject body weight.

7. The method of claim 4 wherein the glucocorticosteroid is cortisol.

8. A method for modifying or resetting the phases of circadian oscillations of the brain which control circadian rhythms of prolactin in the bloodstream of a human patient in need of said modification or resetting comprising:

a) determining the time of day at which the bloodstream level of prolactin peaks in a lean, insulin-sensitive human and the value of said peak level;

b) determining the time of day at which the bloodstream level of prolactin peaks in said patient and the value of said patient's peak prolactin level; and c) administering prolactin to said patient daily to modify or reset the patient's daily prolactin cycle so that it mimics in both phase and amplitude the daily prolactin level cycle of a lean insulin-sensitive human.

9. The method of claim 8 wherein the modification persists after cessation of said prolactin administration.

10. The method of claim 8 wherein prolactin is administered once a day at dosage levels ranging from about 175 micrograms to about 2000 micrograms, per pound of body weight.

11. The method of claim 10 further comprising administering a glucocorticosteroid daily to said patient.

12. The method of claim 11 wherein the prolactin is administered at a first time during a 24 hour period, and glucocorticosteroid is administered at a second time during the same 24 hour period, said glucocorticosteroid being administered at dosage levels ranging from about 175 micrograms to about 2000 micrograms, per pound of body weight.

13. The method of claim 11 wherein said glucocorticosteroid is cortisol.

* * * * *

UNITED STATES PATENT AND TRADEMARK OFFICE
CERTIFICATE OF CORRECTION

PATENT NO. : 5,496,803
DATED : March 5, 1996
INVENTOR(S) : Albert H. MEIER and Anthony H. CINCOTTA It is certified that error appears in the above-indentified patent and that said Letters Patent is hereby corrected as shown below:

On the title page: Item

[75], Inventors: , change "Albert H. Meier; Anthony H. Cincotta, both Baton Rouge, La." to --Albert H. Meier, Baton Rouge, La.; Anthony H. Cincotta, Andover, Ma.--.

Signed and Sealed this

Fourth Day of February, 1997

Attest:

BRUCE LEHMAN

*Attesting Officer*   *Commissioner of Patents and Trademarks*